United States Patent
Williams et al.

[11] Patent Number: 5,977,964
[45] Date of Patent: Nov. 2, 1999

[54] METHOD AND APPARATUS FOR AUTOMATICALLY CONFIGURING A SYSTEM BASED ON A USER'S MONITORED SYSTEM INTERACTION AND PREFERRED SYSTEM ACCESS TIMES

[75] Inventors: Christopher D. Williams, Soquel; Jean M. Goldschmidt Iti, San Jose; Anthony A. Shah-Nazaroff, Santa Clara; E. Michael Watts, Morgan Hill; Kenneth Alan Moore, Fremont; David N. Hackson, Sunnyvale, all of Calif.

[73] Assignee: Intel Corporation, Santa Clara, Calif.

[21] Appl. No.: 09/002,892

[22] Filed: Jan. 5, 1998

Related U.S. Application Data

[63] Continuation-in-part of application No. 08/866,707, May 30, 1997
[60] Provisional application No. 60/019,351, Jun. 6, 1996, provisional application No. 60/024,435, Aug. 22, 1996, provisional application No. 60/024,436, Aug. 22, 1996, provisional application No. 60/024,452, Aug. 27, 1996, and provisional application No. 60/020,580, Jun. 26, 1996.

[51] Int. Cl.⁶ ........................ H04N 7/16
[52] U.S. Cl. ............... 345/327; 348/10; 386/83
[58] Field of Search .................. 345/327; 348/1, 348/10, 5; 455/2, 6.2, 6.3; 386/46, 83; H04N 7/16, 7/173

[56] References Cited

U.S. PATENT DOCUMENTS

| | | | |
|---|---|---|---|
| 5,444,499 | 8/1995 | Saitoh | 348/734 |
| 5,583,560 | 12/1996 | Florin et al. | 348/7 |
| 5,867,205 | 2/1999 | Harrison | 348/1 |
| 5,867,226 | 2/1999 | Wehmeyer et al. | 348/563 |

*Primary Examiner*—Chris Grant
*Attorney, Agent, or Firm*—Blakely, Sokoloff, Taylor & Zafman LLP

[57] ABSTRACT

A method and apparatus for automatically configuring a system based on a user's monitored system interaction and preferred system access times updates a user profile corresponding to the user based at least in part on the monitored user interaction with the system. Preferred system access times of the user are identified based at least in part on the user profile, and the system is automatically configured based at least in part on the user profile and the user's preferred system access times.

14 Claims, 9 Drawing Sheets

Fig. 8

| USER NAME | TELEVISION | | | | | COMPUTER | | AUDIO COMPONENTS | | | |
|---|---|---|---|---|---|---|---|---|---|---|---|
| | CH | VOL | GENRE | BLOCK | SUPP-PROG | INTERNET | AUTO-FEATURE | STATIONS | TYPE | VOL | |
| JOE USER | 2 | o | S | NONE | NONE | GAMES | CLOCK | 750 kHz | J | – | ••• |
| | 5 | + | M | NONE | NONE | SPORTS | BIRTHDAY REMINDERS | 800 kHz | P | • | ••• |
| | 7 | – | M$_V$ | v++ | NONE | | | 1.2 mHz | R | • | ••• |
| | 11 | o | N | NONE | Q | FINANCIAL | | 1.195 mHz | J | • | ••• |
| | ••• | ••• | ••• | ••• | ••• | ••• | ••• | ••• | ••• | ••• | ••• |
| | ••• | ••• | ••• | ••• | ••• | ••• | ••• | ••• | ••• | ••• | ••• |
| ••• | | | | | | | | | | | |

← 800

KEY:
S-SPORTS
M-MUSIC
M$_V$-MOVIES
N-NEWS
Q-QUOTES
P-POP
R-ROCK
J-JAZZ

VOLUME:
"+" - HIGH
"o" - MEDIUM
"–" - LOW

Fig. 9

| MEDIUM | CH | 12AM | 12:30AM | 1:00AM | ... | 10:00PM | 10:30PM | 11:00PM | 11:30PM |
|---|---|---|---|---|---|---|---|---|---|
| CABLE | 1 | ∼ | ∼ | ∼ | • | ∼ | ∼ | ∼ | ∼ |
| | 2 | ∼ | ∼ | ∼ | ∼∼∼∼∼ | ∼ | ∼ | ∼ | ∼ |
| | ... | ... | ... | ... | ... | ... | ... | ... | ... |
| SATELLITE | • | • | • | • | • • • | • • | • • | • • | • • |
| | • | • | • | • | • • • | • • | • • | • • | • • |
| AUDIO | • | • | • | • | • • • | • • | • • | • • | • • |
| | • | • | • | • | • • • | • • | • • | • • | • • |

DAYS OF MONTH 1-31
DAYS OF WEEK M-SU

900

5,977,964

METHOD AND APPARATUS FOR AUTOMATICALLY CONFIGURING A SYSTEM BASED ON A USER'S MONITORED SYSTEM INTERACTION AND PREFERRED SYSTEM ACCESS TIMES

RELATED APPLICATIONS

This is a continuation-in-part of application Ser. No. 08/866,707, filed May 30, 1997, entitled "Method and Apparatus for Automatically Determining and Dynamically Updating User Preferences in an Entertainment System", which claims priority to provisional application No. 60/019,351 by Jean Goldschmidt, Earl Watts and Kathleen Lane, for a Programming Preferences Agent Specification filed on Jun. 6, 1996; provisional application No. 60/024,435 filed on Aug. 22, 1996, for a Television Viewing Behavior Monitor by Jean Goldschmidt, Tony Shah, Christopher Williams and Kathleen Lane; provisional application No. 60/024,436 entitled Entertainment System Which Customizes Its Configuration To A Particular User, filed on Aug. 22, 1996; provisional application No. 60/024,452 entitled Television Personalization, filed on Aug. 27, 1996, by Jean Goldschmidt, Tony Shah, Christopher Williams and Kathleen Lane; and provisional application No. 60/020,580 entitled Customized Television Schedule With Suggested Viewing List, filed on Jun. 26, 1996, by Jean Goldschmidt and Michael Watts. Each of the foregoing provisional applications is commonly assigned to Intel Corporation of Santa Clara, Calif.

BACKGROUND OF THE INVENTION

1. Field of the Invention

The present invention relates to the field of entertainment systems and, in particular, to a method and apparatus for automatically configuring a system based on a user's monitored system interaction and preferred system access times.

2. Background Information

Numerous advances have been made in recent years in the field of entertainment systems. For example, programming guides are now prevalent on many cable systems throughout the country. In one embodiment, these programming guides are offered on a particular channel within the cable broadcast, and provide programming information for the next several hours. More advanced ones of these prior art systems may allow the user to interact with the program guide to manually select a particular program to record or view.

Another example of advances in entertainment systems has been the advent of parental control, wherein a person may "lock out" or require a password for channels that may be unsuitable for certain members of the family. Equally impressive advances have been made in audio devices, video recorders/playback devices, etc. A number of these devices allow a user to manually program the device to record a program given appropriate information regarding the program (channel, date, start time, end time, etc.). Other current systems allow a user to manually "add" and "erase" channels and thereby generate a preferred "channel surfing" order. For example, the user may erase channels 3 and 4 in order to pass directly from channel 2 to channel 5 when channel surfing. However, with these systems the channel surfing order must be manually programmed by a user and must be manually re-programmed by the next user if he or she desires a different order. Typical prior art entertainment systems are not capable of automatically and dynamically configuring the entertainment system in accordance with a user's monitored system interaction (e.g., the channels a user watches and the times of day he or she watches them). Furthermore, typical prior art entertainment systems are not capable of altering their configuration based on what times (e.g., 5:00 pm–8:00 pm) the system is accessed.

Thus, a need exists for a method and apparatus for automatically configuring a system based on a user's monitored system interaction and preferred system access times.

SUMMARY OF THE INVENTION

In accordance with the teachings of the present invention, a method and apparatus for automatically configuring a system based on a user's monitored system interaction and preferred system access times is provided. According to one embodiment, a user profile corresponding to the user is updated based at least in part on the monitored user interaction with the system. Preferred system access times of the user are identified based at least in part on the user profile, and the system is automatically configured based at least in part on the user profile and the user's preferred system access times.

BRIEF DESCRIPTION OF THE DRAWINGS

The present invention will be described by way of exemplary embodiments, but not limitations, illustrated in the accompanying drawings in which like references denote similar elements, and in which:

FIG. 8 illustrates a user profile database according to one embodiment of the present invention; and FIG. 9 illustrates a program database according to one embodiment of the present invention.

DETAILED DESCRIPTION

In the following description, for purposes of explanation, specific numbers, materials and configurations are set forth in order to provide a thorough understanding of the present invention. However, it will be apparent to one skilled in the art that the present invention may be practiced without the specific details. In other instances, well known features are omitted or simplified in order not to obscure the present invention. Furthermore, for case of understanding, certain method steps are delineated as separate steps, however, these separately delineated steps should not be construed as necessarily order dependent in their performance.

Figure 1:
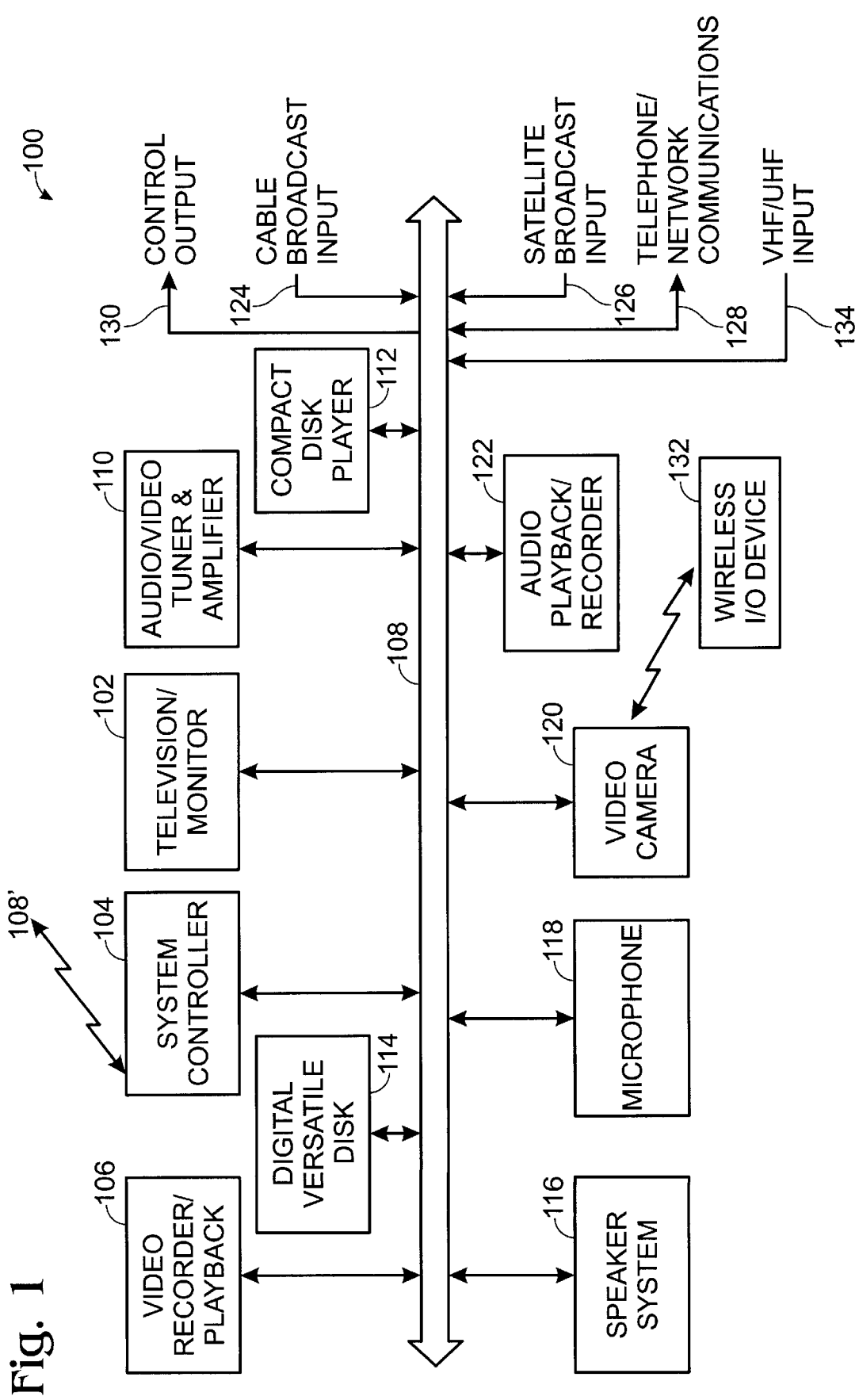
FIG. 1 is a block diagram illustrating a number of components making up an entertainment system in which the present invention may be practiced.

Turning now to FIG. 1, a block diagram is presented illustrating the system components of one example of an exemplary entertainment system in which the present invention may be practiced. As will be discussed in greater detail below system 100 includes system controller 104 which, in one embodiment, is configured to store user profile information which controller 104 develops for each of the users of system 100. In addition, system controller 104 is configured to retrieve and store entertainment programming information available from a wide variety of sources. During operation of system 100, system controller 104 automatically determines which user of a plurality of system users is currently using the system by comparing received inputs and current settings to at least a subset of the user profiles for at least a subset of the plurality of entertainment system users. Having determined which user of the plurality of system users is currently using the system, system controller 104 dynamically configures the operating parameters of system 100 in accordance with the user preference information of the user profile corresponding to the determined entertainment system user, and offers programming/entertainment suggestions, and a host of additional value added features to enhance the user's enjoyment of system 100. In one embodiment, system controller 104 may be a computer system incorporated with the teachings of the present invention, as will be discussed in further detail below. In another embodiment, system controller 104 may be a "set-top" box endowed with the necessary processing power and incorporated with the teachings of the present invention. Regardless of the particular embodiment, system controller 104 may also be referred to as a "convergence system" designed to integrate the world of entertainment systems and computing platforms to achieve the beneficial results discussed in greater detail below.

Although the present invention is described in the context of the exemplary embodiments presented in the figures, based on the descriptions to follow, those skilled in the art will appreciate that the present invention is not limited to these embodiments and may be practiced in a variety of alternate embodiments. Accordingly, the innovative features of the present invention may be practiced in a system of greater or lesser complexity than that of the system depicted in FIG. 1.

As shown, FIG. 1 illustrates but one example of an entertainment system incorporated with the teachings of the present invention. In the illustrated embodiment, system 100 includes television/monitor 102, video recorder/playback device 106, DVD recorder/playback device 114 (DVD is currently used as an acronym for digital video disk and also digital versatile disk to reflect the ability of DVD technology to be used for data other than video), audio/video tuner and amplifier 110, audio playback/recorder device 122 and compact disk player 112, all coupled to a common input/output (I/O) bus 108. It is to be appreciated that the use of the common I/O bus 108 is for ease of explanation in the diagram only, and that a number of alternative means of routing input and output signals may be beneficially employed. For example, audio input and output could be routed with an appropriate number of independent audio "patch" cables, video signals may be routed with independent coaxial cable, and control signals may be routed along a two-wire serial line, or through infrared (IR) communication signals or radio frequency (RF) communication signals.

In addition, system 100 includes speaker system 116, microphone 118, video camera 120 and a wireless input/output control device 132. In one embodiment, wireless I/O control device 132 is an entertainment system remote control unit which communicates with the components of system 100 through IR signals. In another embodiment, wireless I/O control device 132 may be a wireless keyboard and cursor positioning device that communicates with the components of system 100 through IR signals or RF signals. In yet another embodiment, wireless I/O control device 132 may be an I/R remote control device similar in appearance to a typical entertainment system remote control with the added feature of a track-ball, which allows a user to position a cursor on a display of system 100.

At the core of the system is system controller 104 incorporated with the features of the present invention, configured to control a wide variety of features associated with each of the system components. As depicted, system controller 104 is coupled to each of the system components, as necessary, through I/O bus 108. In one embodiment, in addition to or in place of I/O bus 108, system controller 104 may be configured with a wireless communications transmitter (or transceiver), which is capable of communicating with the system components via IR signals or RF signals 108'. Regardless of the control medium, system controller 104 is configured to control each of the entertainment system components of system 100, although it is understood that each of the components may be individually controlled with wireless I/O device 132.

As illustrated in FIG. 1, system 100 can be configured to receive programming input from a wide variety of sources. In one embodiment, for example, system 100 receives programming input from any or all of the following sources: cable broadcast 124, satellite broadcast 126 (e.g., via a satellite dish), very high frequency (VHF) or ultra high frequency (UHF) radio frequency communication of the broadcast networks 134 (e.g., via an aerial antenna), and/or the telephone/computer network interface 128. It will be appreciated by those skilled in the art that each of the sources may be tuned to different channels, stations, numbers, etc. Further, it will be appreciated by those skilled in the art, that cable broadcast input 124, satellite broadcast input 126 and VHF/UHF input 134 may beneficially receive input from digital broadcast programming and digital cable programming.

In addition to programming input, system 100 is also configured with a number of general purpose control outputs 130 which may be configured to control any number of devices. In one embodiment, for example, as system controller 104 configures system 100 to display a movie, it may also dim the lights in the room to a predetermined level to further enhance the viewing environment. Control circuitry which allows a computer system to control, for example, lighting, thermostat settings, and other household appliances are well known in the art and thus will not be described further. In another embodiment, system controller 104 analyzes programming content and configures system 100 to take full advantage of the programming. For example, if a television show is being broadcast in surround sound, system controller 104 determines that program is offered in surround sound and configures system 100 to display the television show in surround sound. If the next show televised on the network is not broadcast in surround sound, system controller 104 determines this and configures system 100 to display the television show in stereophonic or monophonic sound, as appropriate.

Except for the incorporated teachings of the present invention (to be more fully described below), system controller 104 is intended to represent a broad category of computer systems known in the art. An example of such a computer system is a desktop computer system equipped with a high performance microprocessor(s), such as the Pentium® processor, Pentium® Pro processor, or Pentium® II processor manufactured by and commonly available from Intel Corporation of Santa Clara, Calif., or the Alpha® processor manufactured by Digital Equipment Corporation of Manard, Mass.; a number of audio and video input and output peripherals/interfaces for receiving, digitizing and compressing audio and video signals are also known in the art. It is to be appreciated that the housing size and design for system controller 104 may be altered, allowing it to better visually fit into system 100.

It is also to be appreciated that the several entertainment system components depicted in FIG. 1 can be beneficially combined. By way of example, system controller 104 could be integrated into television/monitor 102, DVD 114, or audio/video tuner and amplifier 110.

Figure 2:
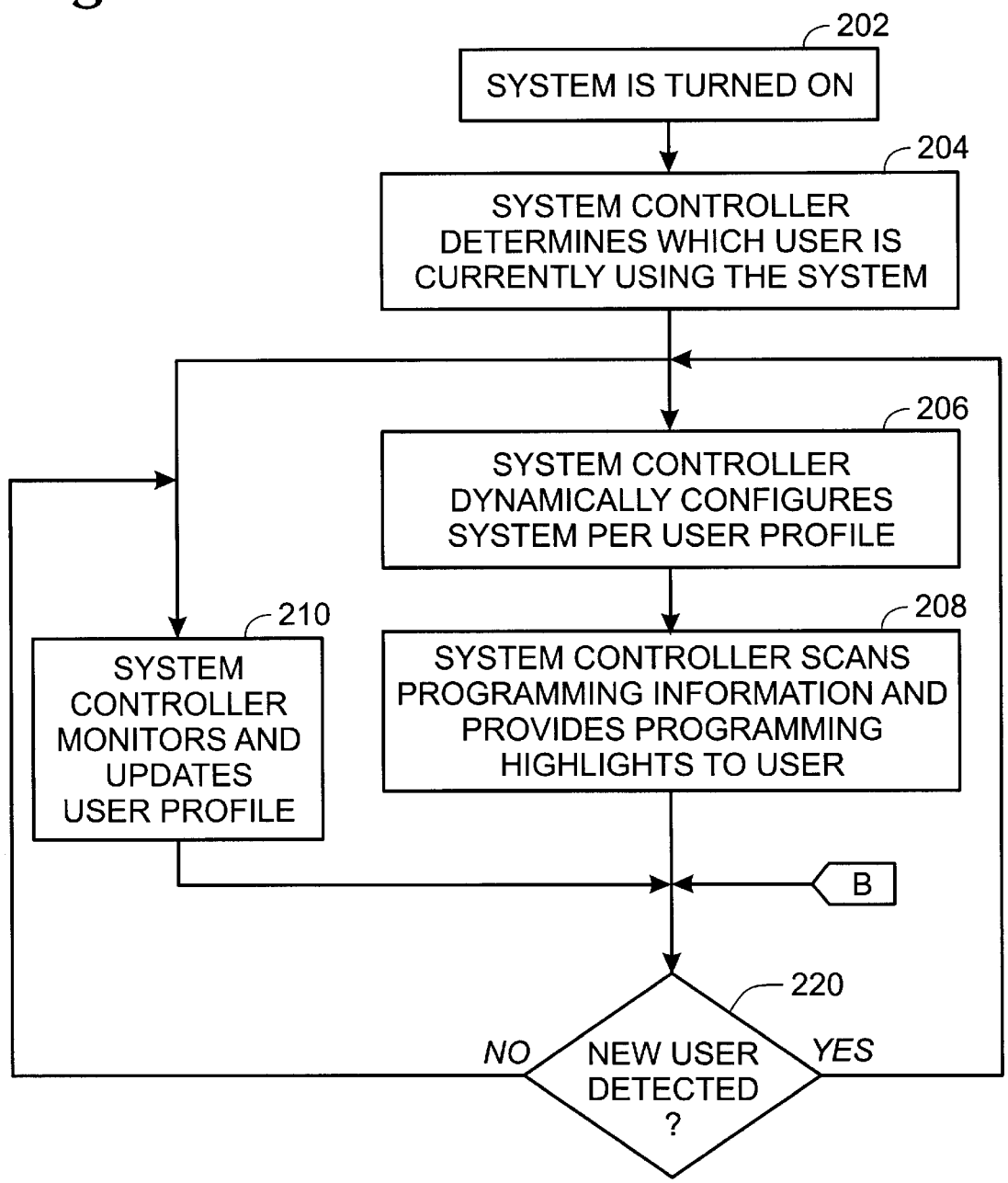
FIG. 2 is a flow chart illustrating the steps followed in dynamically customizing system operating parameters corresponding to user preferences in accordance with one embodiment of the present invention.
Figure 3:
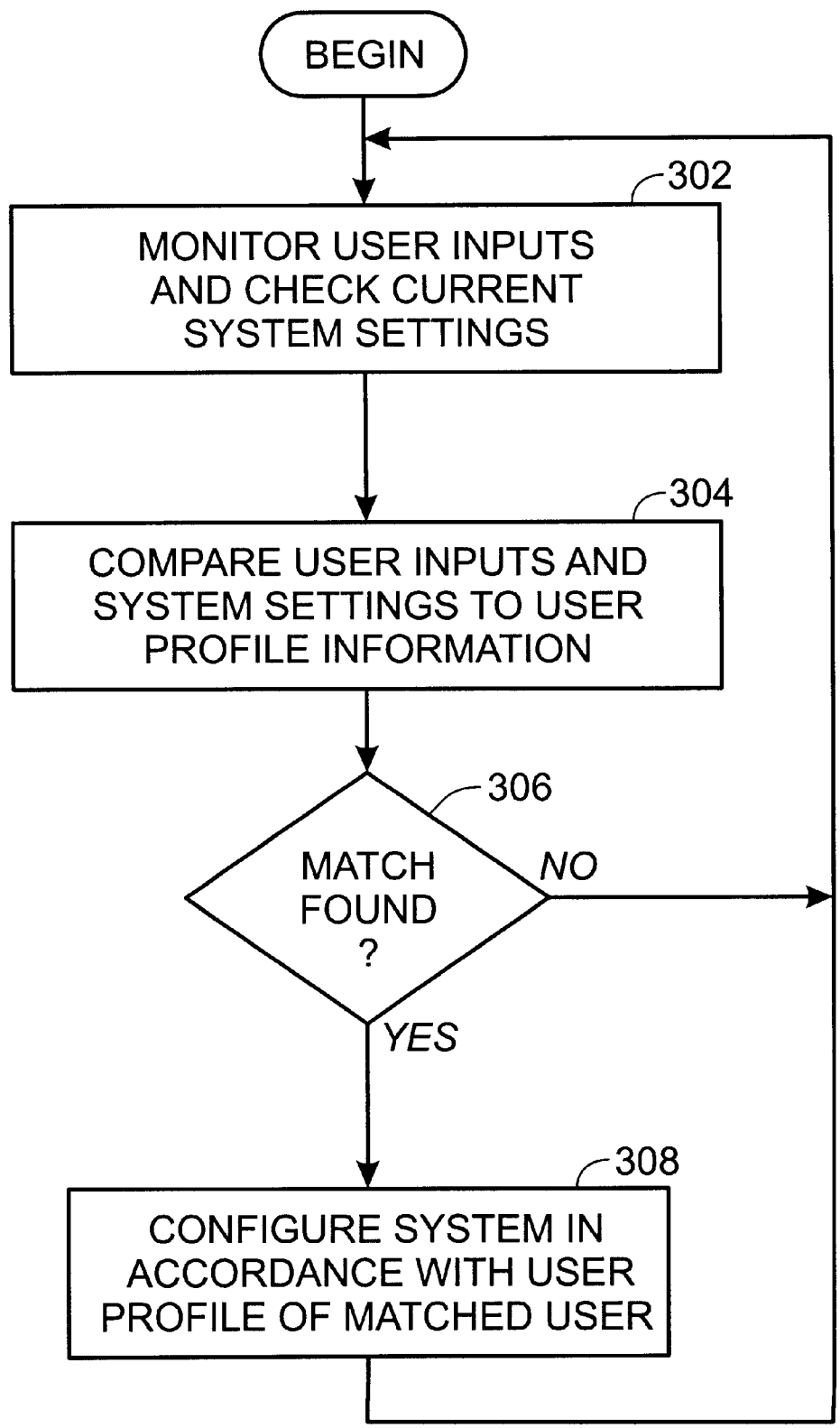
FIG. 3 is a flow chart illustrating the steps followed in determining which user of a plurality of system users is currently using the system according to one embodiment of the present invention.
Figure 4:
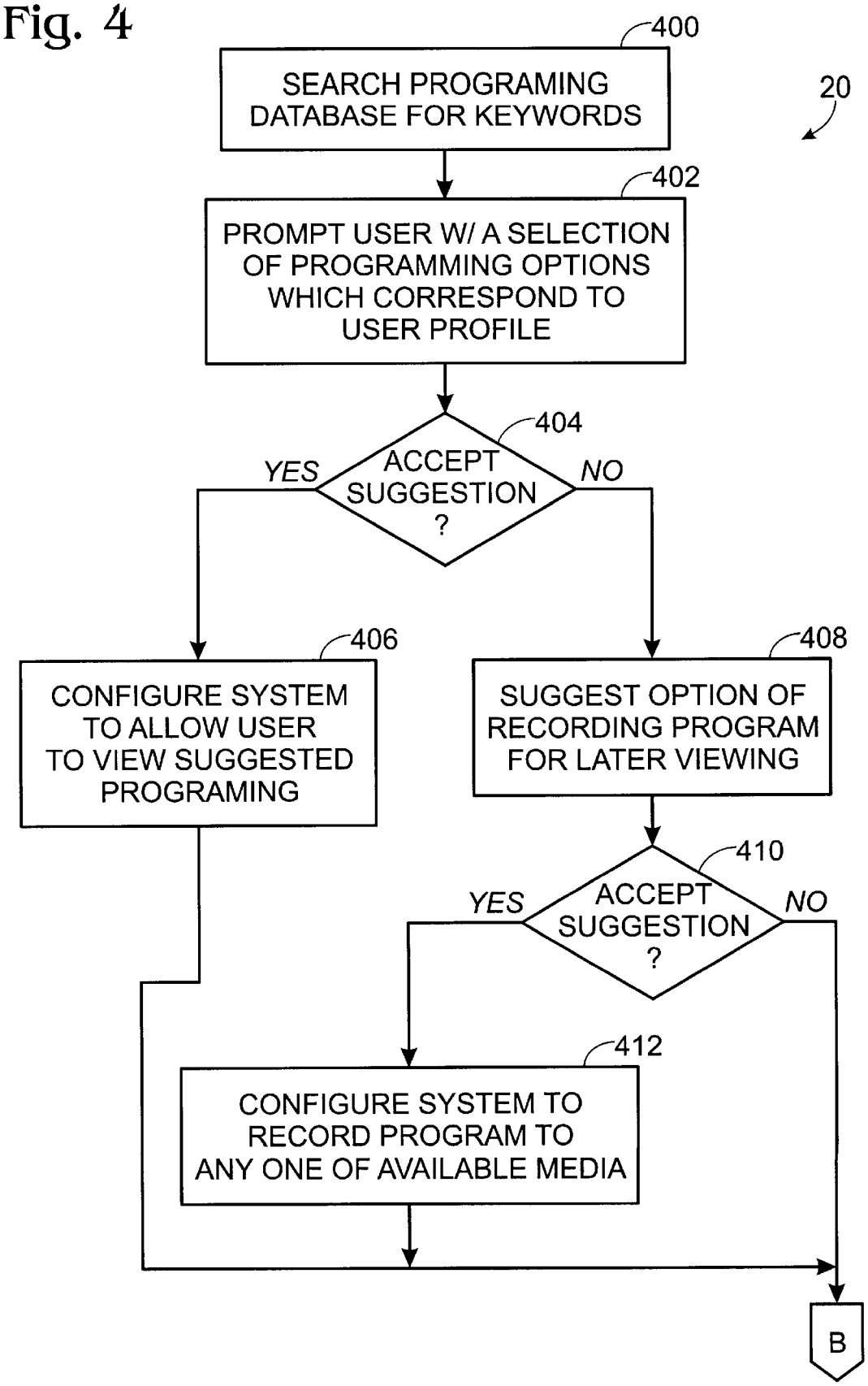
FIG. 4 is a flow chart illustrating the steps followed identifying programming information which might be of interest to a user according to one embodiment of the present invention.

Turning now to FIGS. 2 through 4, flow charts illustrating one embodiment of the method steps of the present invention for automatically determining which of a plurality of users is currently using the system, and automatically configuring the system in accordance with user preference information of the user profile is shown. For ease of explanation, and not limitation, the method of FIGS. 2 through 4 will be developed in the context of an example implementation, wherein a user first begins using system 100, step 202. It is to be appreciated that system 100 provides a number of alternate means by which system 100 may be activated. In one embodiment, the user simply uses wireless I/O device 132 to begin watching television 102. In one embodiment, the user is "surfing" the Internet via system controller 104 and a modem (not shown) coupled to telephone/network communications I/O 128. Regardless of the means by which the user activates system 100, system controller 104 determines which user of a plurality of known system users is currently using system 100, step 204. The method by which system controller 104 determines which user of a plurality of users is currently using system 100 is described more fully below.

Having determined which user of a plurality of users is currently using system 100 in step 204, system controller 104 dynamically configures system configuration settings of system 100 in accordance with the user preference information found in the user profile corresponding to the identified user, step 206. As described in more detail below, this configuration can be based, at least in part, on the user's preferred system access times. That is, when the user prefers to use the system or have the system perform an action on his behalf, such as record a program.

Referring to FIG. 8, depicted therein is one example of user profile database 800. In the illustrated embodiment of FIG. 8, user profile database 800 contains information (user preference information) associated with each of the different media supported in system 100. For example, in the illustrated embodiment of FIG. 8, user profile database 800 includes user preference information related to a television/monitor, a personal computer and audio components. As depicted, for television/monitor 102, user profile database 800 tracks user preferred channels, volume, program genre information, whether to block content information, and whether supplemental programming is requested with a particular channel. In the illustrated embodiment, for example, user profile database 800 includes a profile for the fictitious "Joe User". As illustrated, Joe User's favorite television channel is channel 2, which he enjoys viewing at a moderate volume; he prefers watching sports-type programming, no blocking is required, nor is any supplemental programming requested. With respect to channel 7, Joe enjoys watching movies available on this channel, at low volume, and he wishes to block violent movies. With respect to channel 11, Joe enjoys watching this station for its news coverage, at moderate volume, without the need for blocking, and Joe desires a "window" to be displayed on the television/monitor in which supplemental programming related to stock quotes are to be presented. In one embodiment, system controller 104 retrieves specific stock quotes customized to Joe's portfolio. In one implementation, system controller 104 retrieves the specific stock quotes from a predetermined world wide web site on the Internet via telephone/network interface 128. In an alternate implementation, system controller 104 retrieves general stock quote information from one of the broadcast network television channels. One skilled in the art will appreciate that in one embodiment, user profile database 800 may be stored locally in a storage medium found in system controller 104, while in alternate embodiments user profile database 800 may be stored remotely and accessed by system controller 104 through one of the many input ports of system controller 104.

By way of additional examples, user profile database 800 includes information indicating Joe User's preferred computer settings, including preferred types of Internet sites (e.g., Games, Sports, and Financial), as well as preferred software applications (e.g., a clock and a birthday reminder application). User profile database 800 also includes information indicating Joe User's preferred audio component settings, including preferred radio stations and corresponding music types, is well as preferred listening volumes. In addition, user profile information may be beneficially used to tailor advertising to the current user of the system 100. In one embodiment, for example, as the programming information is made available to system controller 104, a wide variety of advertising segments may be downloaded which conform to the user profiles stored in a particular entertainment system. Accordingly, if system controller 104 determines that a child is using entertainment system 100, it may restrict the advertising to breakfast cereal's and toys, whereas if the current user is an adult system controller may promote advertising for automobiles and home appliances. In another embodiment, system controller 104 may develop a customized news program, actively accumulating news stories that are particularly relevant or of particular interest to the current system user from any of the plurality of programming sources identified above.

It is to be appreciated that a wide range of configurable options can be monitored and stored in user profile database 800. In addition to those illustrated in FIG. 8, additional user preferences which may be stored in user profile database 800 include video controls such as sharpness, contrast, and brightness, audio controls such as surround sound processing types (including Dolby™ Surround, Dolby™ Digital, Dolby™ Surround Pro Logic, Dolby™ 3 Stereo, and THX™), various surround sound processing modes (including both number of channels and type of sound environment to emulate, such as concert hall, rock concert, movie theater, etc.), stereophonic mode, monophonic mode, closed captioning on/off, and preferred display layouts (e.g., window sizes and locations). Additional preference information may also be stored in user profile database 800, including top ten favorite shows, most frequently watched/listened to source(s), most frequently watched/listened to channel(s)/station(s) per source, typical watching/listening periods, favorite genre(s), favorite commercial(s), favorite actor(s)/actress(es). For example, in one embodiment, system controller 104 determines which commercials a user favors by empirically recognizing which commercials get muted, or which commercials are interrupted (e.g., with a change of channel). In another embodiment, system controller 104 may determine which commercials are preferred by a particular user by eliciting feedback from the user whether the user liked the commercial, the commercial genre, etc. (e.g., through the use of an on screen prompt). In one embodiment, these configurable options for audio and video components are stored in user profile database 800 and referenced according to the media source of the signal (e.g., satellite broadcast). By way of example, the user's preferred video and audio settings may differ based on the source of a signal, such as the surround sound processing mode preferences of "concert hall" for one audio station, "rock concert" for a second audio station, and "movie theater" for one of the satellite channels.

In one embodiment of the present invention, user profile database 800 also stores default configuration options for each component. For example, a particular volume level, contrast setting, brightness setting, etc. for television/monitor 102 is stored and used by system controller 104 in the event different channel-specific preferences are not stored in user profile database 800. By way of another example, a particular volume level and station setting for audio/video tuner and amplifier 110 is stored and used by system controller 104 in the event more specific preferences are not stored in user profile database 800.

In one embodiment of the present invention, system controller 104 also provides a television schedule grid which displays the current channel selections for a predetermined period of time (e.g., the next two hours, week, or several weeks). The current program scheduling to be displayed is available from a programming database, as discussed in more detail below with reference to FIG. 9. The display of this television schedule grid is a configurable option which can vary from user to user based on the user's preference. In one embodiment, the television schedule grid displays only those channels which user profile database 800 indicates the current user watches. Additionally, in one embodiment the ordering of the channels on the television schedule grid varies based on the user's preference. In this embodiment, user profile database 800 maintains a record of the time a user spends watching each television channel. Then, when system controller 104 receives a request to view the television schedule grid (e.g., via the user's remote control) it displays the channels in the grid in the order of most frequently watched to least frequently watched. In an alternate embodiment, the television schedule grid displays the channels in the grid based on the genre of programming available during the displayed time period. For example, channel 2 may be Joe User's favorite channel, but if channel 8 is airing a football game while channel 2 is airing a documentary on the history of knitting (not high on the list of Joe User's genre preferences), system controller 104 will display channel 8 before channel 2.

According to another embodiment of the present invention, the television schedule grid displays the programming options available only during a particular time period (s) of the day based on the user's preferred system access times. This time period is the time period, identified by system controller 104 based on user profile database 800, during which the user most frequently watches television. For example, a user may typically watch television only between 6:00 pm and 9:00 pm. Thus, in this embodiment the present invention would display only the programming options available during the 6:00 pm to 9:00 pm time period, even if the grid were to be displayed at 10:00 am.

In one embodiment of the present invention, selection of various programs can be made via the television schedule grid. In this embodiment, a user can select a particular portion of the grid by moving a cursor across the grid to a cell in the grid that contains the title of the program to be selected and then "clicking" the mouse button while the cursor is within the cell. System controller 104 can then ask the user whether the selected program is to be watched or recorded and display or record the program as requested by the user.

Returning to the example implementation of FIG. 2, in parallel to configuring the system configuration of system 100 in step 206, system controller 104 continuously monitors the user interaction with system 100 to update and refine the user preference information stored in user profile database 800 in step 210. In particular, system controller 104 monitors and logs each of the user inputs received by the entertainment system (e.g., volume, color, supplemental programming, time logged on a particular web page, etc.) and updates the user preference information found in the appropriate records of the user profile.

It is to be appreciated that, in order to accurately monitor and log user inputs, system controller 104 needs to be made aware of the user inputs. In one embodiment, input signals (e.g., channel/station changes, volume changes, web page addresses, device programming inputs, etc.) are input to system 100 via system controller 104, which in turn forwards control signals to the appropriate components to perform the desired function. In an alternate embodiment, inputs could be provided to different components of system 100 directly without going through system controller 104. In this embodiment, system controller 104 could receive control signals from the different components which identify the user inputs. Alternatively, in this embodiment system controller 104 could passively monitor wireless signals provided to various components of system 100, such as via wireless I/O device 132, in order to identify user inputs.

Once system 100 has been configured in accordance with the user preference information found in user profile database 800, system controller 104 scans the programming information found in a program database to identify programs which may be of particular interest to the user, based on the user profile, in step 208. The method in which system controller 104 provides appropriate programming suggestions will be described in further detail below. In one embodiment, the program database is part of system controller 104, and is updated periodically by accessing a remote server (not shown) via telephone/network communications 128 or via other mediums such as distributed diskettes or CD ROMs, a vertical blanking interval (VBI) of an analog video signal, or an additional data stream corresponding to a digital video signal (e.g., from a satellite system). In an alternate embodiment, the program database is located on a remote server (not shown), and system controller 104 accesses the remote server when necessary. One example of a program database, suitable for use in the present invention, is depicted in FIG. 9. In the illustrated embodiment of FIG. 9, program database 900 provides programming information corresponding to various media (cable, RF broadcast, satellite, audio programming, etc.), channels available in each medium, program time slots, and the genre of the program in each time slot. This information is then available for each day of the week (Monday–Sunday), and for each day of the month (1–31), as appropriate. For ease of explanation, program database 900 is depicted as a three-dimensional array, however, program database 900 could be implemented using any of a wide variety of conventional data structures.

It is to be appreciated that additional information (not shown) can also be stored for the various channels in program database 900. This additional information includes the length of the program, a program description/synopsis, actors/actresses, director, date of first airing or release, program genre, channel call-sign, rating, critique, etc.

Returning now to FIG. 2, having provided programming suggestions, as appropriate in step 208, system controller 104 continues to monitor user interaction with system 100 until system controller 104 detects a new user, step 220. In the illustrated embodiment, system controller 104 continues to monitor user interaction with system 100 and determine whether a new user is detected until system 100 is turned off.

FIG. 3 illustrates the steps followed by system controller 104 in determining which of a plurality of system users is currently using system 100, in accordance with one embodiment of the present invention. In particular, FIG. 3 illustrates steps 204 and 220 of FIG. 2 in more detail, in accordance with one embodiment of the present invention. As depicted, the method begins with system controller 104 monitoring user interaction with system 100 and checking current system settings, step 302. This monitored user information is stored in a behavior log, as discussed in more detail below. In step 304, system controller 104 compares the information contained in the behavior log as well as the current system settings with user preference information for at least a subset of the plurality of entertainment system users. In one embodiment, the plurality of user profiles are stored locally, in system 100, and the entire user profile is used to determine which user is using the entertainment system. In an alternate embodiment, system controller 104 may load into a memory a select subset of user preference information for a first subset of the plurality of entertainment system users, and, if a match is not found, loads a subset of user preference information from a subsequent subset of the plurality of entertainment system user profiles until a match is found. Information available on the known system users is contained in a user profile database (e.g., user profile database 800) which may reside locally within system 100, or may reside at remote location. In one implementation, system controller 104 uses only that information in the behavior log which has been stored since the later of system controller 104 last being turned on and system controller 104 last identifying a particular user. In step 306, system controller 104 identifies whether the information of the behavior log matches that of the data for any of the known system users. In one embodiment, system controller 104 calculates a user metric for the information in the behavior log and the current system settings as well as for each of the known system users. If there is greater than a predetermined probability that the information in the behavior log matches the user profile of one of the known users, system controller 104 determines that a match has been made and, in step 308, configures system 100 in accordance with the user preference information of the user profile database 800.

In one embodiment, the user metric takes into account the current settings in system 100 for each user configurable option as stored in user profile database 800, such as television channel, current volume setting, current audio station, program genre, etc. It is to be appreciated that in order to identify some information, such as program genre, system controller 104 may need to access program database 900 of FIG. 9 to identify which program and thus the program genre of the television channel currently being viewed. In other embodiments, this supplemental information may be provided in the broadcast itself as Intercast™ information, or in the VBI, or using other enhanced television data mechanisms.

To generate the metric, in one embodiment of the present invention, each of the configurable options is given a different predetermined weight and the weighted values are added together. By way of example, the television channel being viewed may be given a higher weight than the volume of the channel. This sum of weighted values is compared to a predetermined value and, if the sum exceeds the predetermined value, then the system controller 104 considers a match to be found. In one embodiment, the predetermined weights are dynamic, allowing the weight for a particular option to change as the duration of that option remains unchanged. For example, the weight of the television channel being viewed may be much higher if the channel has remained unchanged for a few minutes, indicating that a user is actually watching that channel, rather than if the channel changes every few seconds, indicating that a user is simply "flipping" through channels. That is to say, the weight given to the different configurable options is determined empirically over time, allowing system controller 104 to improve the accuracy of its ability to quickly identify which user is currently using system 100.

In one embodiment of the present invention, the user is prompted for verification of the match in step 306 by system controller 104. For example, system controller 104 may provide a window on television/monitor 102 wherein a number of pictures of possible system users are displayed, wherein the first picture displayed is that which system controller 104 has identified as the most likely system user, requesting that the user affirmatively respond (e.g., via remote control or voice command) when their picture is displayed; or alternatively, system controller 104 may provide an audio prompt in the form of a question, e.g., "Is that you, Joe?". If the match is verified as being accurate, then system controller 104 proceeds to configure the system in step 308. Otherwise, system controller 104 returns to step 302 to continue monitoring user interaction with system 100.

In one embodiment of the present invention, system controller 104 allows the users to initially "train" the system with specific user preferences. This training allows the users to initially select some, or all, of their preferences. In one implementation, this training is through a direct input of specific options such as preferred channels, volume settings, program genre, etc. In an alternate implementation, the training of the system is done indirectly via an on-screen questionnaire(s), wherein the user is asked to select from a list of program genre (science fiction, sports, documentaries, etc.) that the user enjoys watching. System controller 104 then translates the responses to the questionnaire(s) to different configuration options available in system 100.

In one embodiment of the present invention, system controller 104 uses a pre-programmed default setting until a user match is found in step 304. In an alternate embodiment, system controller 104 uses "conservative" (e.g., low volume settings, display only non-blocked television channels, etc.) user preference options stored in user profile database 800 until a user match is found. For example, if parental controls are selected to block out several channels for one user but not for the other users, system controller 104 uses those parent controls as the default preferences until a user match is found.

In alternate embodiments of the present invention, different mechanisms may be beneficially employed to identify the current user of system 100 other than that described above. For example, in one embodiment the user of system 100 speaks into a microphone of system 100 (e.g., to activate system 100). System controller 104 compares the audio input from the user to pre-stored audio samples from the plurality of possible users and identifies which of the pre-stored samples is closest to the audio input to identify the user. One example of suitable audio recognition software is SpeakerKey, commonly available from ITT Industries of Fort Wayne, Ind. Another suitable audio recognition development software is Speech Print ID, commonly available from Voice Print Systems of Dallas, Tex. In another alternate embodiment, a video image of the user of system 100 is scanned using one or more video cameras of system 100. System controller 104 compares the scanned image of the user to pre-stored visual scans of the plurality of possible users and identifies which of the pre-scanned images is closest to the scanned image of the current user to identify the user. One example of suitable video recognition software is True Face CyberWatch, commonly available from Miros Inc., of Wellesley, Mass.

Having determined which user of a plurality of entertainment system users is currently using system 100, system controller 104, in one embodiment, presents the user with a number of programming suggestions which most closely align with the user profile of the particular user, step 208 of FIG. 2. FIG. 4 illustrates the method steps followed by system controller 104 to identify programming which might be of particular interest to the user according to one embodiment of the present invention. System controller 104 first accesses a program database searching for keywords which match user profile preferences, step 400. That is, in accordance with the teachings of the present invention, system controller 104 accesses a program database, such as program database 900, and searches through the available program information for keywords that match genre information, for example, contained in the user profile of the current user. In the illustrated embodiment of FIG. 4, having accessed program database 900, system controller 104 determines from the available programming information all programs which match the user's preferences for programming genre as found in user profile database 800. For example, if Joe User appears from his user profile to be a fan of the University of Michigan football team, system controller 104 searches through program database 900 for University of Michigan football games. If none are found, system controller 104 may preferably default to sporting events in general.

Having developed a list of programming suggestions in step 400, system controller 104 prompts the system user, in an interactive pop-up window, with the list of programming suggestions, step 402. The user may select one of the suggested programming options through, for example, wireless I/O device 132, or elect to forego the suggestion and continue to watch the program on the current channel, step 404. If the user selects one of the suggestions in the interactive pop-up window in step 404, system controller 104 configures system 100 to allow the user to view the chosen program, in accordance with the user profile, step 406.

In one embodiment of the present invention, user profile database 800 also includes storage for user-defined requests. System controller 104 allows individual users to input requests for particular suggestions. These requests can be for specific titles of shows/movies or keywords, the request may include wildcards (e.g., any shows with "star" in the title), and can also be negative (e.g., no shows with "star" in the title). Given a particular search request, system controller 104 searches the programming information each time it receives updated programming information (via an on-line service, diskette, etc. as discussed above), and prompts the user with the found program information in step 402. The user is then able to select viewing and/or recording of the program.

If, however, the user elects to forego the suggested programming in step 404, system controller 104 may then prompt the user with the option of recording one of the suggested programs in step 408. If the user elects to record one of the program suggestions, system controller 104 configures system 100 to record the program selection to any one of the available recording media. In one embodiment, for example, system controller 104 may configure video recorder/playback device 106 with the requisite information necessary (date, channel, start time, end time, etc.) to record the program on video tape. In an alternate embodiment, system controller 104 may record the program selection on a mass storage device which is part of system controller 104 itself (see, for example, FIG. 6 below). If, however, the user elects to forego recording any of the program suggestions made in step 410, system controller simply continues to monitor and update user preferences, in accordance with FIG. 2. Although presented in the context of a video broadcast, one skilled in the art will appreciate that the foregoing is equally applicable to each of the plurality of programming input described earlier.

In one embodiment of the present invention, system controller 104 repeats the steps of FIG. 4 each time a new user is detected, thereby providing current programming suggestions to the new user, as discussed above with reference to FIG. 2. In addition, in one embodiment of the present invention, system controller 104 also repeats the steps of FIG. 4 periodically. This allows new suggestions to be provided to the user. In an alternate embodiment, system controller 104 may provide programming suggestions to a user well in advance (e.g., a couple of days or weeks), with options for issuing reminder prompts, to record the program, or to forego further prompts of the program. In another embodiment, rather than waiting for a prompt from the user, system controller 104 may automatically provide a customized programming guide tailored to the user profile of the current user.

Figure 5:
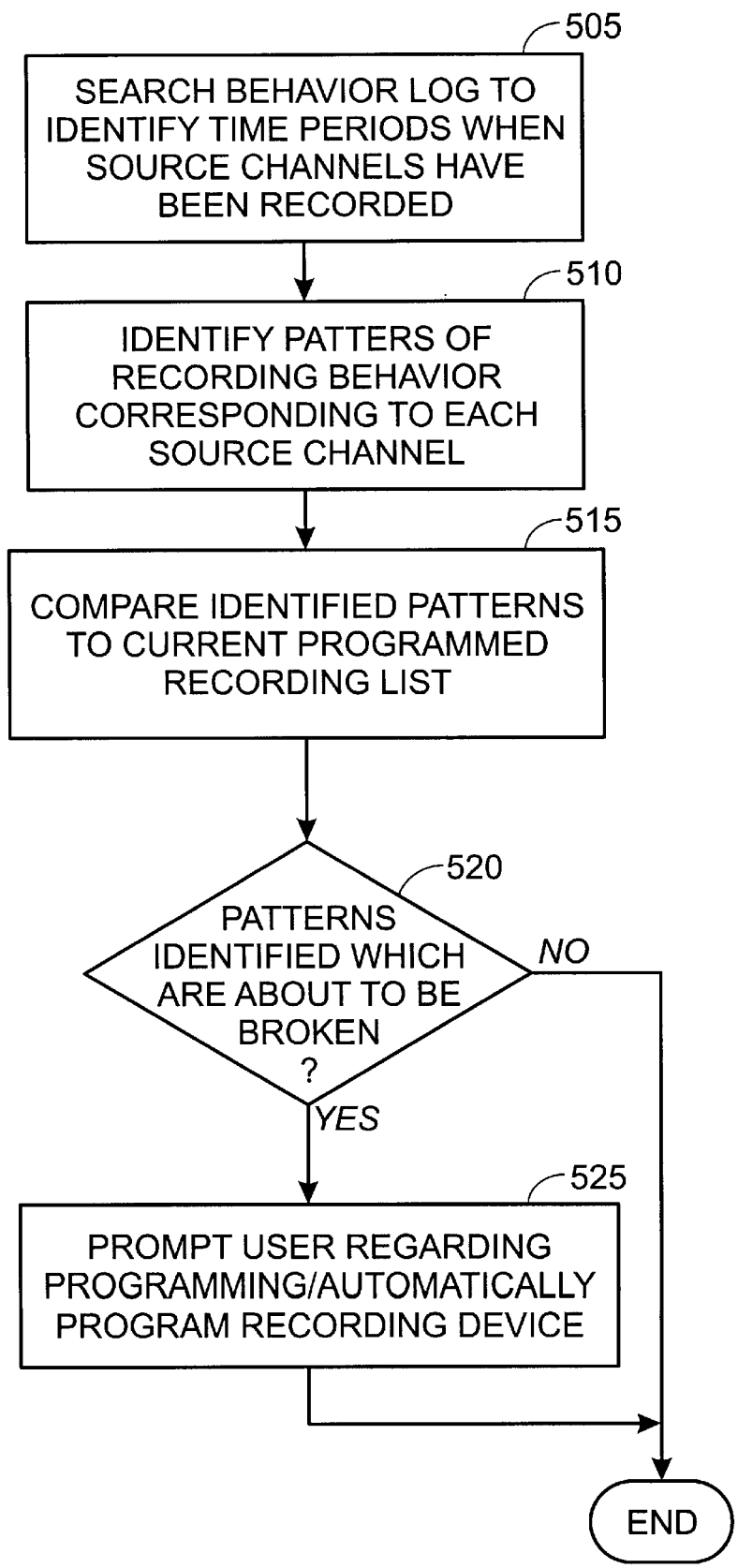
FIG. 5 is a flow chart illustrating the steps followed in determining whether previous recording habits are about to be broken according to one embodiment of the present invention.

Having determined which user of a plurality of entertainment system users is currently using system 100, system controller 104, in one embodiment, determines whether previous program recording habits are soon to be broken. FIG. 5 illustrates the method steps followed by system controller 104 to determine whether previous recording habits are about to be broken.

In carrying out the steps of FIG. 5, system controller 104 relies on the existence of a record of the user's program recording habits. In the illustrated embodiment, this record is maintained in a behavior log, such as behavior log 724 of FIG. 7 discussed in more detail below. Each time a user either records from a programming source or programs a recording device to record from a programming source at a future time, system controller 104 updates the behavior log with the programming source, the channel the programming source is tuned to, the time, and the duration of the recording. System controller 104 also relies on a current programmed recording list. In the illustrated embodiment, system controller 104 generates the current programmed recording list from the behavior log by searching the log for entries for recordings which indicate a record time later than the current time. Alternatively, the programmable recording list could be maintained separate from the behavior log, or could be provided to system controller 104 by the recording device itself.

System controller 104 first searches the behavior log to identify time periods when source channels have been recorded, step 505. In the illustrated embodiment, system controller 104 identifies each time period and the corresponding source and channel from which the user has recorded a program within a previous period of time. In one embodiment, this previous period is the three months preceding the current time. However, alternate embodiments could use longer or shorter preceding periods.

System controller 104 then identifies patterns of recording behavior corresponding to each of the source channels, step 510. System controller 104 can be programmed to identify any of a wide variety of patterns, such as recording the same time period (e.g., 1:30 pm to 2:00 pm, or 6:00 am to 7:00 am) of a particular channel every day for at least a certain number (e.g., two) of immediately preceding days. Or alternatively the same time period for each of at least x out of y immediately preceding days (e.g., three out of five). Or alternatively the same time period each week (e.g., 7:00 pm to 8:00 pm every Sunday). It is to be appreciated that a wide variety of additional patterns can also be identified within the spirit and scope of the present invention.

Once the patterns are identified, system controller 104 compares the identified patterns to the current programmed recording list, step 515, and checks whether there are patterns identified which are about to be broken, step 520. A pattern is about to be broken if there is no entry in the recording list which indicates that the next logical recording time, according to the pattern, is going to be recorded. Thus, if the pattern indicates that a particular channel is typically recorded 5:00 pm to 5:30 pm every day, but there is no indication in the record list that that channel will be recorded 5:00 pm to 5:30 pm tomorrow, then the pattern is potentially about to be broken. System controller 104 will go a predetermined period of time into the future to determine whether the patterns are about to be broken. This period of time could be one day, one week, one month, etc. In one implementation the period of time into the future is dependent on the pattern itself. For example, system controller 104 may go two days into the future for a pattern that indicates daily recording, and may go one week into the future for a pattern that indicates weekly recording.

If none of the patterns are potentially about to be broken, then no further actions are taken by system controller 104 at this time. However, if there is a pattern which is potentially about to be broken, then system controller 104 either prompts the user as to whether the user wants to record the channel at the time indicated by the pattern, or alternatively automatically programs the device to record, step 525. System controller 104 can also access a programming database, such as database 714 of FIG. 7, to identify what program will actually be broadcast at the time the pattern indicates, and thus provide the user with a name of the program rather than merely a channel number. In one implementation, if the user responds to a prompt indicating he or she does want to record the program, then system controller 104 programs a recording device, such as video recorder/playback device 106.

In one embodiment of the present invention, system controller 104 repeats the steps of FIG. 5 each time a new user is detected, thereby checking for broken program recording habits for each new user. Additionally, in one embodiment of the present invention, system controller 104 also repeats the steps of FIG. 5 periodically, at either regular or irregular intervals.

Figure 6:
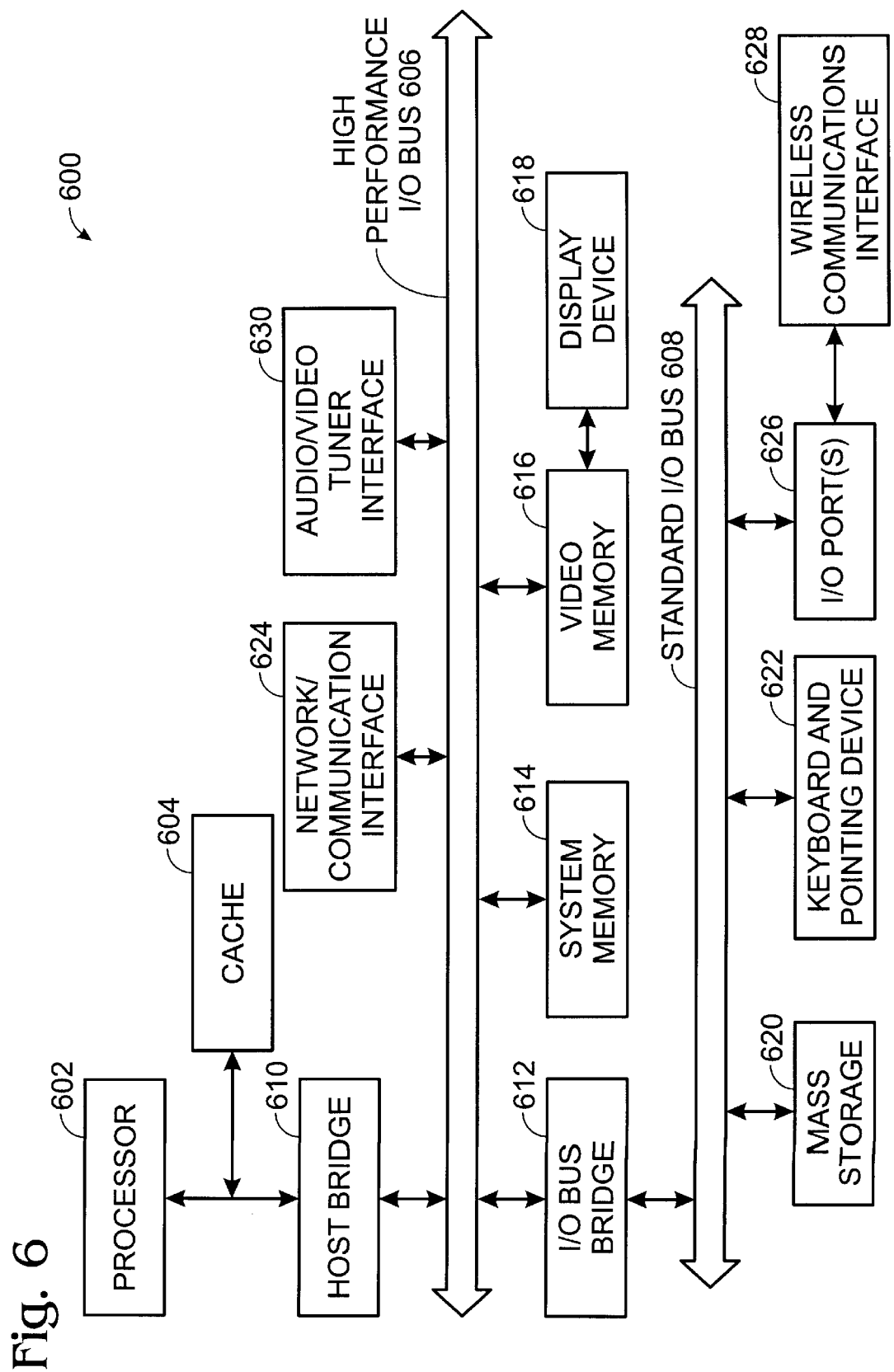
FIG. 6 is a block diagram illustrating an example computer system incorporating the teachings of one embodiment of the present invention.

Turning now to FIG. 6, a block diagram is presented illustrating an example system controller incorporated with the teachings of the present invention. In one implementation, system controller 600 may be used as system controller 104 of FIG. 1. In the illustrated embodiment, system controller 600 includes processor 602 and cache memory 604 coupled to each other as shown. Additionally, system controller 600 includes high performance input/output (I/O) bus 606 and standard I/O bus 608, as shown. Host bridge 610 couples processor 602 to high performance I/O bus 606, whereas I/O bus bridge 612 couples high performance I/O bus 606 to standard I/O bus 608. Coupled to high performance I/O bus 606 are network/communication interface 624, system memory 614, audio/video interface board 630 and video memory 616. In turn, display device 618 is coupled to video memory 616. In one embodiment, display device 618 is television 102 of FIG. 1. Coupled to standard I/O bus 608 are mass storage device 620, keyboard and pointing device 622, and I/O ports 626. As illustrated, wireless communications interface 628 is coupled to I/O port 626. In one embodiment, wireless communications interface 628 is an IR transceiver for receiving IR signals from and sending IR signals to the components of system 100. In one embodiment, wireless communications interface 628 is an RF transceiver for receiving RF signals from and sending RF signals to the components of system 100.

In one embodiment of the system controller 600, keyboard and pointing device are coupled to standard I/O bus 608 with a serial communication interface cable, while in alternate embodiments it may be communicatively coupled with an infrared (IR) interface or a radio-frequency (RF) interface.

With continued reference to FIG. 6, elements 602–630 perform their conventional functions as known in the art. In particular, network/communication interface 624 is used to provide communication between system 600 and any of a wide range of conventional networks, such as Ethernet, token ring, the Internet, etc. Similarly, audio/video interface board 630 is used to receive broadcast communications from any of a wide range of conventional broadcast media such as RF broadcasts, satellite broadcasts, cable broadcasts, etc. Mass storage device 620 is used to provide permanent storage for the data and programming instructions to implement the above described functions, whereas system memory 614 is used to provide temporary storage for the data and programming instructions when executed by processor 602. I/O ports 626 are one or more serial and/or parallel communication ports used to provide communication between additional peripheral devices which may be coupled to hardware system 600. Collectively, the elements coupled of system controller 600 are intended to represent a broad category of hardware systems, including but not limited to general purpose computer systems based on the Pentium® processor, the Pentium® Pro processor, or the Pentium® II processor commonly available from Intel Corporation of Santa Clara, Calif.

It is to be appreciated that various components of system controller 600 may be rearranged. For example, cache 604 may be on-chip with processor 602. Alternatively, cache 604 and processor 602 may be packed together as a "processor module", with processor 602 being referred to as the "processor core". Furthermore, mass storage device 620, keyboard and pointing device 622, and/or display device 618 and video memory 616 may not be included in system controller 600. Additionally, the peripheral devices shown coupled to standard I/O bus 608 may, in alternate embodiments, be coupled to high performance I/O bus 606; in addition, in some implementations only a single bus may exist with the components of system controller 600 being coupled to the single bus. Furthermore, additional components may be included in system controller 600, such as additional processors, storage devices, or memories.

In one embodiment, the innovative features of the present invention discussed above may be implemented as a series of software routines run by system controller 600 of FIG. 6. These software routines run a plurality or series of instructions to be executed by a processor, such as processor 602 in system controller 600. Initially, the series of instructions are stored on a storage device, such as mass storage device 620. It is to be appreciated that the series of instruction may be stored on any conventional storage device, such as a diskette, CD ROM, magnetic tape, DVD, laser disk, ROM, flash memory, etc. It is also to be appreciated that the series of instruction need not be stored locally, and could be received from a remote storage device, such as a server on a network, via network/communication interface 624. The instructions are copied from the storage device, such as mass storage device 620, into system memory 214 and then accessed and executed by processor 602. In one embodiment, these software routines are written in the C++ programming language. It is to be appreciated, however, that these routines may be implemented in any of a wide variety of programming languages. In alternate embodiments, the present invention may be implemented in discrete hardware or firmware. For example, an application specific integrated circuit (ASIC) could be programmed with the above described functions of the present invention.

Figure 7:
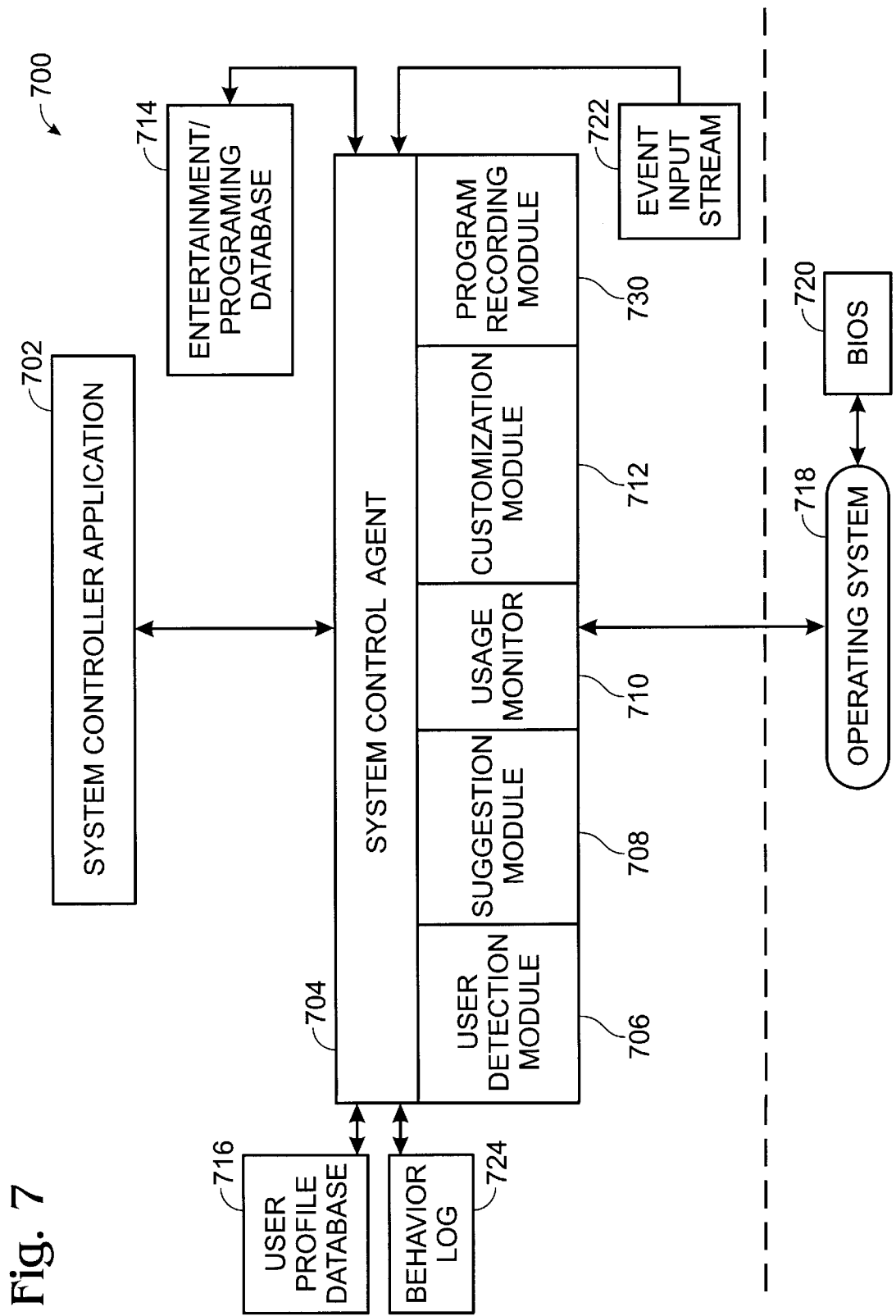
FIG. 7 is a block diagram illustrating the software elements according to one embodiment of the present invention.

FIG. 7 is a block diagram illustrating the software elements according to one embodiment of the present invention. In particular software architecture 700 is shown comprising a system controller application 702, system control agent 704 with associated user profile database 716 and program information database 714, and an operating system 718 with associated drivers. In particular, system controller application 702 interfaces with system control agent 704 and provides the user interface for system controller 104 of FIG. 1.

System control agent 704 includes user detection module 706, suggestion module 708, usage monitor 710, customization module 712, and program recording module 730. As illustrated, system control agent 704 is coupled to and able to obtain information from user profile database 716, program information database 714, and behavior log 724. User detection module 706 performs the steps of determining which of a plurality of system users is currently using system 100 as described above. Suggestion module 708 performs the steps of identifying programming which might be of interest to a user as described above. Usage monitor 710 monitors the user inputs and current system settings and records the information in records of user profile database 716. Customization module 712 controls the setting of the various configurable options in accordance with the preferences of the identified user as discussed above. Program recording module 730 performs the steps of identifying patterns of recording behavior and prompting a user or automatically programming certain programs as described above.

Behavior log 724 is a storage for log information detailing the usage of system 100. In the illustrated embodiment, system control agent maintains records in behavior log 724 for each component of system 100 detailing, as appropriate, which channel/station was watched/listened to by which users during which time periods of each day. The time increments for the time periods may vary, reasonably ranging up to five minutes. Additionally, in the illustrated embodiment, system control agent 704 accesses programming database 714 to identify, for each time period recorded for a user in behavior log 724, which program was watched/listened to by the user. In alternate embodiments, additional information is also maintained in behavior log 724 by system control agent 704. This additional information can include which Intercast™ data, if any, was viewed, changes in volume such as decreases or muting, which programs were recorded, which programming sources were recorded at what times, which programs were suggested by system controller 104 and whether or not the suggested programs were watched, which web pages were accessed and both when and how long they were accessed, which links were taken from which web pages, etc.

Additionally, according to one embodiment of the present invention, system control agent 704 periodically transmits a copy of the behavior log to a remote server for data compilation purposes. In this embodiment, system control agent 704 can request demographic information from each user to be transmitted with the behavior log to allow for better analysis of the log information contained in the behavior log.

System control agent 704 also receives event input stream 722 which identifies the user inputs to the various components of system 100. As discussed above, these user inputs may be made directly to system control agent 704 by the user or the components or system 100, or may be received indirectly from wireless signals transmitted to the components of system 100 by the user.

Basic input/output system (BIOS) 720 provides an interface between operating system 718 and the various input/output (I/O) devices coupled to the hardware system. Operating system 718 is a software service which provides an interface between BIOS 720 and system control agent 704 as well as other software applications, if any, being executed by system controller 104. Operating system 718 provides an interface, such as a graphical user interface (GUI), between the user and the system controller. According to one embodiment of the present invention, operating system 718 is the Windows™ 95 operating system, available from Microsoft Corporation of Redmond, Wash. However, it is to be appreciated that the present invention may be used with any other conventional operating system, such as other versions of Microsoft Windows™ (for example, Windows™ 3.0, Windows™ 3.1, Windows™ NT, or Windows™ CE), Microsoft DOS, OS/2, available from International Business Machines Corporation of Armonk, N.Y., the Apple Macintosh Operating System, available from Apple Computer Incorporated of Cupertino, Calif., the NeXTSTEP® operating system available from Apple Computer Incorporated, or the UNIX operating system, available from Santa Cruz Operations of Santa Cruz, Calif.

In the discussions above, several examples of configurable options are given in describing the operation of the present invention. It is to be appreciated that these are only examples of the options which can be used with the present invention and that a wide range of options for the components of FIG. 1 can be automatically configured in accordance with the present invention.

Also in the discussions above, several references are made to prompting a user for input. It is to be appreciated that alternate embodiments may not include these prompting and that system controller 104 of FIG. 1 can automatically perform various functions without prompting. By way of example, if system controller 104 identifies a particular program which may be of interest to a particular user, system controller 104 can record the program without prompting the user.

It is also to be appreciated that although the discussions above discuss taking various actions for the current system user, the present invention can also automatically take actions on behalf of users not currently using the system. By way of example, in one embodiment system controller 104 of FIG. 1 identifies a program(s) which may be of interest to a user(s) other than the current user and automatically records that program. Subsequently, the user for which the program was recorded can be notified of the recording the next time the user is using the system 100.

In one embodiment of the present invention, various automatically configured options discussed above can be viewed and modified by users. In this embodiment, users are able to access their preferences on user profile database 800 of FIG. 8 and add to, subtract from, and/or modify their recorded preferences.

Thus, the present invention automatically configures a system based on a user's monitored system interaction and preferred system access times. As discussed above, the present invention advantageously identifies preferred system access times of a user and automatically configures the system based on these times. In one embodiment, this system configuration includes advantageously identifying a pattern of program recording which is about to be broken and either notifying the user of the program about to break the pattern or automatically recording the program.

While the method and apparatus of the present invention has been described in terms of the above illustrated embodiments, those skilled in the art will recognize that the invention is not limited to the embodiments so described. The present invention can be practiced with modification and alteration within the spirit and scope of the appended claims. For example, although depicted as separate components, any number of the components of system 100 may be incorporated into multipurpose devices (e.g., a television/monitor/video cassette recorder/playback device). Further, system controller 104 may well be incorporated into any of the system components, and may not include all of the elements of FIG. 6, or may, alternatively, include additional elements. Accordingly, the description is to be regarded as illustrative instead of restrictive on the present invention.

Thus, a method and apparatus for automatically configuring a system based on a user's monitored system interaction and preferred system access times has been described.

We claim:

1. A method comprising:

updating a user profile corresponding to the user based at least in part on monitored user interaction with a system;

identifying preferred system access times of the user based at least in part on the user profile;

automatically configuring the system based at least in part on the user profile and the user's preferred system access times;

detecting a plurality of corresponding time periods during which a programming device is recording a source;

identifying that the recording device has not been programmed to record the source during a first time period which corresponds to the plurality of corresponding time periods; and prompting a user as to whether the user wishes to record the source during the first time period.

2. The method of claim 1, further comprising:

providing a viewing guide which indicates television viewing options available to a user; and wherein the automatically configuring comprises automatically presenting the television viewing options in the viewing guide in accordance with the user profile.

3. The method of claim 2, wherein the providing comprises displaying the viewing guide to the user.

4. The method of claim 1, wherein two of the plurality of corresponding time periods comprise a same period of time on two consecutive days.

5. The method of claim 1, wherein the automatically configuring comprises providing a viewing guide which indicates television viewing options that are available to a user only during a period of time indicated by the user profile as being when the user is likely to be viewing programming.

6. A machine-readable medium having stored thereon a plurality of instructions, designed to be executed by a processor, for implementing a function to:

update a user profile corresponding to a user based at least in part on monitored user interaction with a system;

identify preferred system access times of the user based at least in part on the user profile;

automatically configure the system based at least in part on the user profile and the user's preferred system access times;

detect a plurality of corresponding time periods during which a programming device is recording a source;

identify that the recording device has not been programmed to record the source during a first time period which corresponds to the plurality of corresponding time periods; and prompt a user as to whether the user wishes to record the source during the first time period.

7. The machine-readable medium of claim 6, wherein the function is further to:

provide a viewing guide which indicates television viewing options available to a user; and wherein the automatically configuring comprises automatically presenting the television viewing options in the viewing guide in accordance with the user profile.

8. The machine-readable medium of claim 7, wherein the providing comprises displaying the viewing guide to the user.

9. The machine-readable medium of claim 6, wherein two of the plurality of corresponding time periods comprise a same period of time on two consecutive days.

10. The machine-readable medium of claim 6, wherein the automatically configuring comprises providing a viewing guide which indicates television viewing options that are available to a user only during a period of time indicated by the user profile as being when the user is likely to be viewing programming.

11. An apparatus for use in a system, the apparatus comprising:

a user profile database which stores information corresponding to a user's system usage;

a usage monitor to update the user profile based at least in part on monitored user interaction with the system;

a customization module to identify preferred system access times of the user based at least in part on the user profile, and to automatically configure the system based at least in part on the user profile and the user's preferred system access times; and a recording module operative to,
  detect a plurality of corresponding time periods during which a programming device is recording a source,
  identify that the recording device has not been programmed to record the source during a first time period which corresponds to the plurality of corresponding time periods, and
  prompt a user as to whether the user wishes to record the source during the first time period.

12. The apparatus of claim 11, wherein the customization module is further operative to provide a viewing guide which indicates television viewing options available to a user and to automatically present the television viewing options in the viewing guide in accordance with the user profile.

13. The apparatus of claim 11, wherein two of the plurality of corresponding time periods comprise a same period of time on two consecutive days.

14. The apparatus of claim 11, wherein the customization module is further operative to provide a viewing guide which indicates television viewing options that are available to a user only during a period of time indicated by the user profile as being when the user is likely to be viewing programming.

* * * * *

UNITED STATES PATENT AND TRADEMARK OFFICE
CERTIFICATE OF CORRECTION

PATENT NO. : 5,977,964

DATED : November 2, 1999

INVENTOR(S) : Williams et al.

It is certified that error appears in the above-identified patent and that said Letters Patent is hereby corrected as shown below:

Title page, item [75], should read --

Inventors: Christopher D. Williams, Soquel;

Jean M. Goldschmidt "Iti' *should read* --Iki--, San Jose;

Anthony A. Shah-Nazaroff, Santa Clara;

E. Michael Watts, Morgan Hill;

Kenneth Alan Moore, Fremont;

David N. Hackson, Sunnyvale, all of Calif.

Signed and Sealed this

First Day of May, 2001

Attest:

NICHOLAS P. GODICI

*Attesting Officer*  *Acting Director of the United States Patent and Trademark Office*